(12) United States Patent
Savard et al.

(10) Patent No.: US 9,140,542 B2
(45) Date of Patent: Sep. 22, 2015

(54) CALIPER COATING MEASUREMENT ON CONTINUOUS NON-UNIFORM WEB USING THZ SENSOR

(75) Inventors: Stephane Savard, Vancouver (CA); Adam Krolak, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 760 days.

(21) Appl. No.: 13/444,767

(22) Filed: Apr. 11, 2012

(65) Prior Publication Data

US 2013/0204577 A1    Aug. 8, 2013

Related U.S. Application Data

(60) Provisional application No. 61/596,595, filed on Feb. 8, 2012.

(51) Int. Cl.
| | |
|---|---|
| *G01B 11/06* | (2006.01) |
| *G01N 21/3581* | (2014.01) |
| *G01N 21/3586* | (2014.01) |

(52) U.S. Cl.
CPC ............ *G01B 11/06* (2013.01); *G01B 11/0625* (2013.01); *G01B 11/0691* (2013.01); *G01N 21/3581* (2013.01); *G01N 21/3586* (2013.01)

(58) Field of Classification Search
CPC .......... G01B 11/06; G01B 11/00; G01B 9/00; G01N 21/3563; G01N 21/89; G01N 21/3586
See application file for complete search history.

(56) References Cited

U.S. PATENT DOCUMENTS

| | | | |
|---|---|---|---|
| 2,580,200 A | * | 12/1951 | Shrimpton .................... 264/460 |
| 4,999,509 A | | 3/1991 | Wada |
| 5,604,581 A | | 2/1997 | Liu |
| 5,959,735 A | | 9/1999 | Maris et al. |

(Continued)

FOREIGN PATENT DOCUMENTS

JP    2010533300 T    10/2010

OTHER PUBLICATIONS

PCT/CA2013/000066 Search Report and Written Opinion Dated May 14, 2013.

(Continued)

*Primary Examiner* — Sujoy Kundu
*Assistant Examiner* — Alvaro Fortich
(74) *Attorney, Agent, or Firm* — Cascio Schmoyer & Zervas (57) ABSTRACT

An analytical model simulates the propagation of radiation through a coated continuous web where layer thickness and refractive index, as variables, determine the speed and direction of transmitted radiation. The model predicts characteristics of transmitted radiation based on characteristics of incident radiation and initially assigned values for layer thicknesses. Coating thickness(s) are ascertained in a process whereby incident radiation of known characteristics is directed onto a coated web and thereafter, actual measurements of transmitted radiation are compared to predicted characteristics. Using a fitting algorithm, the assigned thickness(es) of the layer(s) of the model are adjusted and the process repeated until the actual and predicted values are within desired limits at which time, the assigned thickness(es) represent the measured calipers. Radiation measurements are obtained using terahertz time-domain spectroscopy apparatus that creates a continuous reference whereby a sample pulses' phase and amplitude can be tracked and corrected.

20 Claims, 3 Drawing Sheets

(56) References Cited

U.S. PATENT DOCUMENTS

| | | |
|---|---|---|
| 6,242,739 B1 | 6/2001 | Cherkassky |
| 7,199,884 B2 | 4/2007 | Jasinski |
| 7,280,231 B2 | 10/2007 | Yoshizawa |
| 7,609,366 B2 | 10/2009 | MacHattie |
| 2004/0202799 A1* | 10/2004 | Bauer et al. ............ 428/1.3 |
| 2006/0045807 A1 | 3/2006 | Zhang et al. |
| 2008/0037031 A1* | 2/2008 | Cole et al. ............ 356/601 |
| 2009/0128799 A1* | 5/2009 | MacHattie et al. ......... 356/5.05 |
| 2010/0003904 A1* | 1/2010 | Duescher ............ 451/259 |
| 2010/0024999 A1* | 2/2010 | Haran et al. ............ 162/198 |
| 2010/0282970 A1* | 11/2010 | Haran et al. ............ 250/339.07 |
| 2011/0267600 A1* | 11/2011 | Ouchi et al. ............ 356/51 |
| 2012/0049070 A1 | 3/2012 | Mousavi |
| 2012/0304756 A1* | 12/2012 | White et al. ............ 73/150 A |

OTHER PUBLICATIONS

Mousavi et al., Simultaneous composition and thickness measurement of paper using terahertz time-domain spectroscopy., Applied Optics, vol. 48, No. 33, Nov. 20, 2009.

Eugene Hecht, Optics, 2d. edition, Addison-Wesley Publishing Co., Inc. 1987 pp. 373-378.

* cited by examiner

CALIPER COATING MEASUREMENT ON CONTINUOUS NON-UNIFORM WEB USING THZ SENSOR

REFERENCE TO RELATED APPLICATIONS

This application claims priority under 35 U.S.C. §119(e) to co-pending application No. 61/596,595 filed Feb. 8, 2012, which is incorporated herein by reference

FIELD OF THE INVENTION

The present invention generally relates to techniques for determining the thickness, basis weight and related properties of coatings and film layers that employ terahertz spectroscopy measurements.

BACKGROUND OF THE INVENTION

Industrial production of continuous web materials often requires measurement of caliper or basis weight (weight per area unit) for testing and control purposes. For example, in the case of manufacturing coatings, co-extruded plastics, and related multi-layer products, it is often necessary to measure the caliper or basis weight of each of the layers and/or coats. Standard means for determining the caliper of continuous web coatings include, for instance, differential weigh techniques that rely on nuclear or x-ray measurements. This non-contacting scheme employs dual scanners, each equipped with a sensor, that measure the web weight before and after the coating procedure, with the difference being the coating weight. An analogous dual scanner method is the contacting, differential caliper measurement where subtraction of the web caliper before and after the coating procedure yields the coating weight. Finally, infrared radiation detection uses a distinctive IR signature of the coating to detect and measure coating weight.

The utility of these prior art caliper measurement techniques is restricted by a number of drawbacks. Two-scanner differential systems are prohibitively expensive and require excessive space for accommodating both scanners. Furthermore, the technique itself is not reliable for detecting relatively thin coatings that are applied onto a thick base material. Indeed, dual-scanner measurements often yield calculated coating thicknesses with significant errors. Variability of the base layer is another source of error in dual-scanner systems. To compensate for this variability, dual-scanner systems often include same-spot software that compares measurement results obtained by both scanners from the same spots on the moving web. Unfortunately, the scanners do not remain perfectly aligned and their inability to follow the same spot renders the measurement useless especially when the scanners are measuring a traveling web whose thickness is not uniform in the machine direction. It has been demonstrated that conventional dual scanner systems when measuring a thin polymer coating on a baseboard can exhibit an error that is larger than the measured thickness of the coating. Finally, IR sensing is sometimes impossible to implement due to the high IR attenuation in the measured material or lack of distinctive IR signatures that would allow for differentiation of the coating material. The art is in need of an accurate and repeatable technique for measuring the thickness and related properties of coatings and films that are formed on continuous, traveling non-uniform webs.

SUMMARY OF THE INVENTION

The present invention is based in part on the development of an analytical model that describes the propagation of terahertz radiation pulse through a coated web and especially through the coating and base substrate layers of a continuous web sample material. As radiation travels through the layers, its direction(s) and speed(s) of travel are influenced by, among other things, the thicknesses of the layers and their refractive indices. Accordingly, the mathematical relationships used in the model incorporate layer thickness and layer refractive index as variables to predict how incident radiation behaves as it is transmitted through the coated web. Given that incident and transmitted radiation can be measured and the refractive indices can be initially ascertained or measured, the thickness(s) of the coating(s) in the sample are ascertained in an iterative process whereby incident electromagnetic radiation of known characteristics is directed to a coated web and thereafter, actual measurements are compared to predicted transmitted radiation characteristics. The assigned thickness (es) of the layer(s) of the model are adjusted and the process repeated until the actual measurement and predicted transmitted electromagnetic radiation value are within desired limits at which point, the assigned thickness(es) represent the measured caliper values.

The caliper measurement is particularly accurate and precise when implemented with terahertz time-domain spectroscopy (THz-TDS) that creates a continuous set of reference pulses whereby a sample pulses' phase and amplitude can be tracked and corrected. The invention can be implemented with an apparatus that preferably employs two sensor heads and is equipped with means for measuring the z-distance between the sensor heads. In operation, a sample being analyzed, such as a travelling web having non-uniform thickness, is positioned between the two sensor heads. By measuring the z-distance and THz signals in real time, the THz signals can be corrected to enhance the spectrometer measurement precision. The non-contact caliper coating measurements are practically insensitive to variations in the basis weight, thickness or other physical parameters of the base substrate such as paper on which the coating is applied.

Accordingly, in one aspect, the invention is directed to a method of measuring the thickness of a coating on a coated continuous web that includes the steps of:

(a) developing an analytical model of the coated continuous, web having one or more coating layers and a substrate layer wherein the model expresses the transmission of an electromagnetic field through the coated continuous web as a function of (i) the thickness of each coating layer, (ii) the thickness of the substrate layer, (iii) the refractive indices of each coating layer and of the substrate which values are initially assigned, and (iv) angle of incident of terahertz radiation onto the coated continuous web;

(b) establishing a sample measurement for the coated continuous web sample by employing a time-domain terahertz spectroscopy apparatus, that includes an emitter that generates pulses of radiation and a detector that receives pulses of radiation, by a technique which includes the steps of:

(i) positioning a beam splitter along an optical path between the emitter and the detector to form reference radiation pulses and sample radiation pulses that are directed to the sample and the reference radiation pulses do not interact with the sample;

(ii) positioning a first mirror to reflect sample radiation pulses to the detector; and (iii) positioning a second mirror to reflect reference radiation pulses to the detector and using the reflected radiation pulses to monitor fluctuations in phase and amplitude of the reference radiation pulses;

(c) establishing a reference measurement for the coated continuous web sample with the time-domain spectroscopy by executing steps (b)(i), (b)(ii) and (b)(iii) without placement of any sample for measurement; and (d) comparing the sample measurement to the reference measurement and iteratively assigning values for the thickness of the coating and the thickness of the substrate layers based on the model defined in step (a) so as to achieve a best-fit relationship between the sample measurement and the reference measurement to thereby determine the thickness of the coating.

In another aspect, the invention is directed to an apparatus for analyzing a coated continuous web sample, having one or more coating layers and a substrate layer, to measure the thickness of a coating on the continuous web, that includes:

means for establishing sample measurement data for the coated continuous web sample that employs a time-domain terahertz spectroscopy device;

means for establishing reference measurement data for the coated continuous web sample that employs the time-domain terahertz spectroscopy device; and electronic data processing means programmed and operatively connected for processing the sample, measurement data and the reference measurement data wherein the data processing means, is programmed to compare the sample measurement data to the reference measurement data and to iteratively assign values for the thickness of the coating and the thickness of the substrate layer based on an analytical model of the coated continuous web so as to achieve a best fit relationship between the sample measurement data and the reference measurement data to thereby determine the thickness of the coating.

DETAILED DESCRIPTION OF THE PREFERRED EMBODIMENTS

Figure 1:
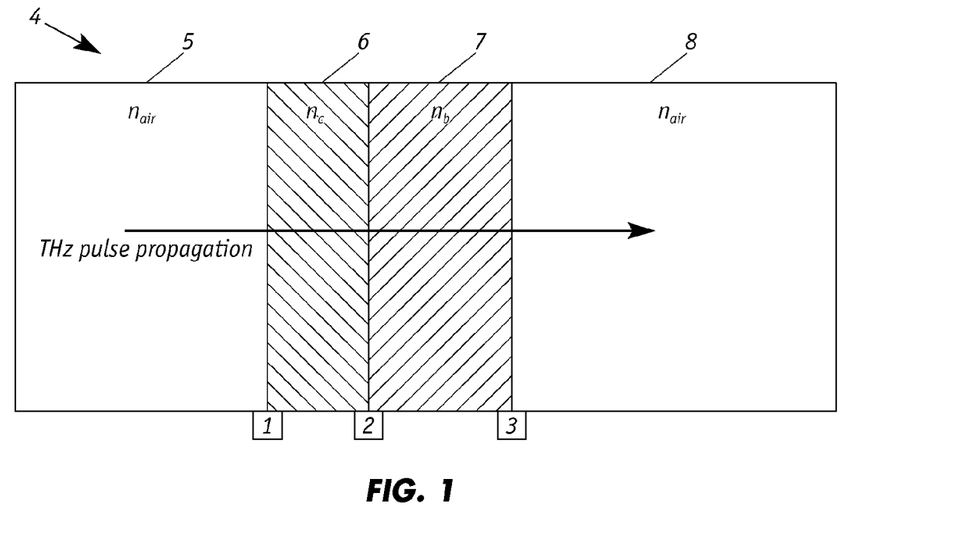
FIG. 1 is an analytical model for a coated board depicted as a four layer optical system.

FIG. 1 depicts a model representing the coated board 4 as a multilayer optical system with four layers consisting of air 5, a coating material 6, a base material or board 7 and finally air 8. The layers have respective refractive indices denoted $n_{air}$, $n_c$ and $n_b$. As an electro-magnetic field E of a terahertz pulse propagates through the system, it encounters three different boundaries between the layers denoted as 1, 2, and 3, respectively, that modify the electric and magnetic fields.

To describe the THz electro-magnetic field interaction in this system, the ABCD matrix analysis (*Optics, Eugene Hecht*, 2d edition, Addison-Wesley Publishing Co., Inc., 1987, p. 373-378) was used and it was assumed that the THz beam can be viewed as a plane wave. Note that the formalism for Gaussian beam can be adapted. Thus, at a boundary, the relation between the electric (E) and magnetic (H) fields is given by the characteristic matrix M, defined by layer i and i+1:

$$\begin{bmatrix} E_i \\ H_i \end{bmatrix} = M_i \begin{bmatrix} E_{i+1} \\ H_{i+1} \end{bmatrix} \quad \text{Eq. 1}$$

$M_i$ is a 2 by 2 matrix define by the wave number k, the thickness of the layer d, and the angle of the field in the layer as respect to the boundary ($\theta_{i+1}$):

$$M_i = \begin{bmatrix} \cos(kd) & \frac{j\sin(kd)}{Y_{i+1}(\theta_{i+1})} \\ j\sin(kd)Y_1(\theta_{i+1}) & \cos(kd) \end{bmatrix} \quad \text{Eq. 2}$$

Where j is the imaginary number (to avoid confusion with the index i) and $Y_{i+1}(\theta_{i+1}'$, a function defined by $$Y_{i+1}(\theta_{i+1}) = \sqrt{\frac{\varepsilon_o}{\mu_o}} \, n_{i+1} \cos(\theta_{i+1}) \quad \text{Eq. 3}$$

When the electric field is not in the plane of incidence, $n_i+1$ is the refractive index of the layer i+1. So, in the case of a multilayer system, the characteristic matrix M of the system is given by the product between all characteristic matrix at each boundaries $M_i$:

$$M = M_i M_{i+1} M_{i+2} \ldots = \begin{bmatrix} m_{11} & m_{12} \\ m_{21} & m_{22} \end{bmatrix} \quad \text{Eq. 4}$$

where the $m_{ij}$ are the matrix elements. In time-domain terahertz measurement, the THz electric field without any sample or coated board $E_o$ is preferably measured first. Hereafter, $E_o$ will be referred as the incident electric field $E_i$ in the system. Because an application of the model is for representation of the transmitted electric field $E_t$, the relation between the $E_i$ and $E_t$ is given by the transfer function I as follows:

$$t = \frac{E_o}{E_t} = \frac{2Y_o(\theta_o)}{Y_o(\theta_o)m_{11} + Y_o(\theta_o)Y_t(\theta_t)m_{12} + m_{21} + Y_t(\theta_t)m_{22}} \quad \text{Eq. 5}$$

The indices o and t for the Y function (Eq. 3) correspond respectively to the initial and final layers where the THz beam propagates. In this case, both layers are air. In a preferred specific application to optimize sensor sensitivity, the THz pulse goes through the coated board twice so that the final transfer function is equation 5 squared. If the board thickness is unknown, preferably a sufficient contrast between the coating and the base material is established in order for the technique to yield good results. The minimal contrast depends on the sensor sensitivity. In one implementation of the model and apparatus, the coating refractive index $n_c$ is preferably kept constant with frequency while the board refractive index $n_b$ is assumed to be like paper (see Applied Optics, vol. 48, no. 33, p. 6541-6546). These refractive indices are used in the equations 2 and 3. Because of the subtlety of the THz time-domain technique in detecting the path length difference to the reference pulse, the phase kd in equation 2 should be adjusted accordingly. Instead of using $n_c$ or $n_b$ alone to define the wave number, $(n_c-1)$ or $(n_b-1)$ is used which is precisely the path length difference to vacuum or air. With the present invention, by incorporating $n_c$, $n_b$, Eo and Et in a non-linear least squares fitting algorithm, the coating caliper can be extracted accurately. Note that although the incident radiation is shown in FIG. 1 to be normal to the coating, it is understood that the angle can be an oblique angle and the analytical model adjusted accordingly. Indeed, the angle can be measured initially and the appropriate model that is already programmed into a processor is selected to calculate the coating thickness. Once the thickness is determined, the basis weight and related properties can also be calculated using standard techniques with density data. The caliper coating measurement technique is particularly suited for gauging continuous webs where each layer in the coating or substrate layer is fabricated from paper, board, plastic, polymer, natural rubber, metal, natural fiber and/or synthetic fiber.

Figure 2:
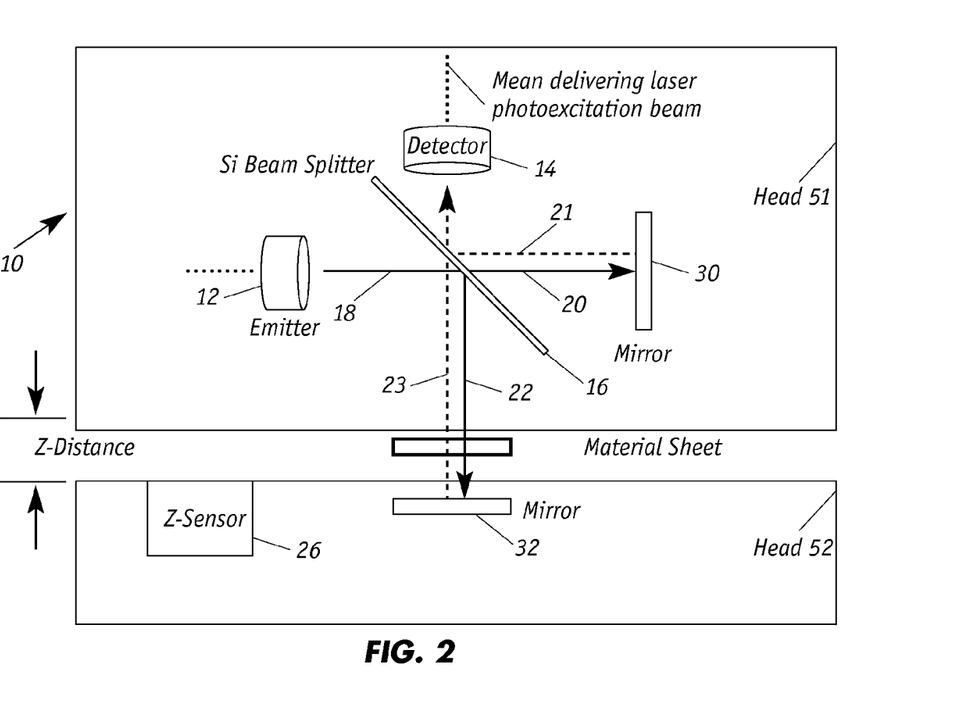
FIG. 2 is a representation of an exemplary THz or near THz-TDS transmission-based sheet measurement system.

FIG. 2 illustrates a continuous real time referencing generating device 10 that is positioned between an emitter 12 and a detector 14 of a time-domain spectrometer. Device 10 is particularly suited for establishing sample and reference measurements for a coated sample. The device includes a beam splitter 16 which splits incidental light 18 from emitter 12 into reflected light 22 and transmitted light 20. The transmitted light 20 is reflected back as light 21 by flat mirror 30 through beam splitter 16 before being received by detector 14. Reflected light 22 is transmitted through a sample 40 and thereafter reflected as light 23 by flat mirror 32 back toward the beam splitter 16 where it is transmitted into detector 14. In the case where this device 10 augments a terahertz spectrometer, the emitter and detector can be, for example, photoconductive antennae. For terahertz radiation, a preferred beam splitter comprises a thick piece of high resistivity (>10,000 O-cm) silicon slab. The thickness of the beam splitter is selected to be large enough so that reflections from the back surface thereof lie outside the measurement window. If a thinner beam splitter is used, the pulse shape will look different since multiple reflections from the backside are included in the window. In principal either configuration can be employed with the present invention. A thicker beam splitter is preferred because it is less prone to vibrate. A high resistivity silicon slab is particularly suited for use as a beam splitter as it has a high refractive index with acceptable absorption in terahertz frequencies. Alternatively, sapphire or polyethylene could be used as the beam splitter although they have higher absorption than that of silicon.

In a preferred embodiment, device 10 includes an upper head or module 51 that houses emitter 12, detector 14 and mirror 30 and a lower head 52 that houses mirror 32. The gap or displacement distance "z" between sensor heads 51, 52 through which the coated non-uniform continuous web sample 40 traverses can vary particularly when the dual sensor heads are in motion as part of a scanner. To account for this z "wander" and therefore the varying length of radiation traveled, the gap separation can be continuously measured. Dynamic measurements can be achieved with conventional devices, such as, for example, a displacement sensor 26, which employs inductive or magnetic measuring devices. Distance signals from z measurements can be communicated to a processor that calculates the time delay based on the z measurements and generates time delay signals. While the terahertz time-domain spectroscopy-based device 10 is illustrated in the transmission mode, it is understood that the invention is also applicable in the reflection mode.

In operation, laser pulses are directed to emitter 12 and detector 14, respectively. (A continuous wave photoconductor can be used instead.) Initially, a terahertz radiation pulse is generated by the photoconductive antenna emitter and is incident on silicon beam splitter 16 at a 45 degrees angle resulting in two pulses traveling in perpendicular directions. One pulse is transmitted through sample 40 whereas the other pulse is used to track the fluctuations in time and amplitude. Since the two pulses are generated at the same time and position, their phases and amplitudes correlate very strongly and this correlation is used to correct measurement errors. This method is particularly suited for fiber optic based time domain terahertz spectrometers where the bending of fibers and temperature fluctuations could have strong adverse effects in precision in amplitude and phase measurements. Only one detector is required although multiple detectors can be employed.

Figure 3:
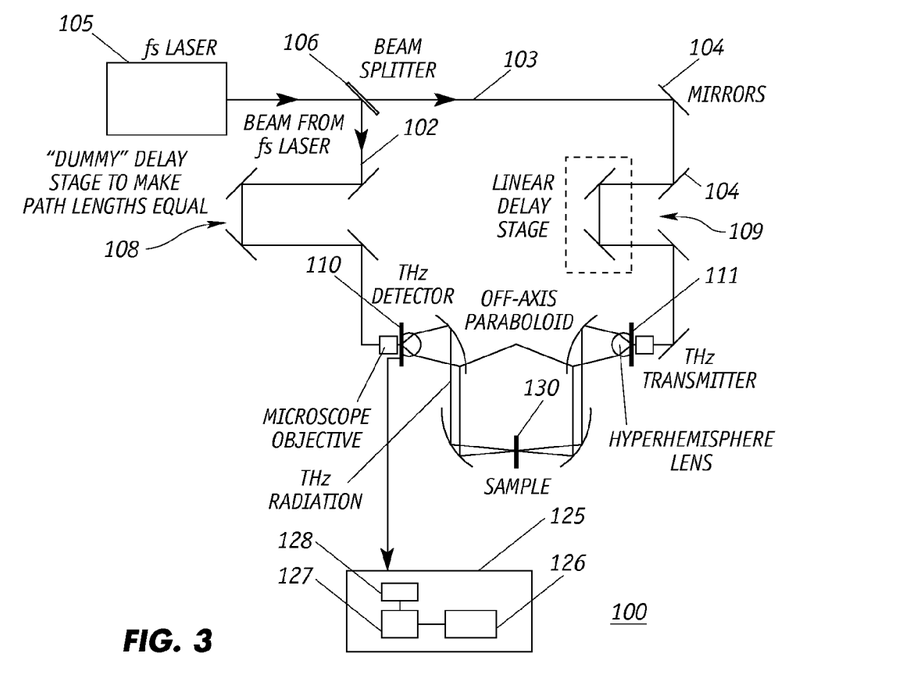
FIG. 3 depicts a device for generating continuous referencing (CR) in time-domain spectroscopy.

The continuous real time referencing generating device 10, configured as depicted in FIG. 2, but without separate heads 51 and 52, was incorporated into a THz or near THz-TDS transmission-based sheet measurement system 100 as shown in FIG. 3. It has been demonstrated that with this THz-TDS system 100, jitter limits the measurement precision of the system. It is expected that implementation of the constant referencing technique will significantly enhance its precision. System 100 comprises a near THz or THz generator including at least one pulsed laser source (e.g. femtosecond (fs) laser) 105 for emitting a beam of optical pulses. A beam splitter 106 splits the optical beam into two beams, a reflected beam 102 and a transmitted beam 103. The reflected beam 102 is directed to reflective delay comprising optics 108 including a "dummy" delay stage. The purpose of the dummy delay is to make both the source (transmitter) and receiver (detector) arms of the THz-TDS system 100 have nominally equal optical path lengths; this results in the source and receiver fs-pulses being derived from the same original fs-pulse. The intention of the dummy delay is to minimize noise. However this dummy delay is not generally required and the THz-TDS system 100 can be also generally operated without it in certain applications.

The transmitted beam 103 is directed via mirrors 104 to delay comprising optics 109 shown as linear delay stage. The delay comprising optics 108 and 109 are configured to make the optical path length of the reflected beam 102 to the detector 110 be nominally equal to the optical path length of the transmitted beam 103 to the near THz or THz transmitter 111.

The near THz or THz transmitter 111 includes a transmit antenna operable for emitting THz or near THz radiation pulses having a frequency between 0.05 THz and 50 THz at a sample location on the sheet material. The THz transmission antenna will generally have a bias voltage applied to it (not shown), which can be modulated be used for the utilization of a lock-in detection scheme in system 100. The detector 110 includes a receiver antenna operable to receive near THz or THz radiation transmitted by the location on the sample 130 that is irradiated by the incident radiation. Embodiments of the invention are not limited to using photoconductive antennae as described herein. For example, other methods such as optical rectification using crystals such as Zinc Telluride (ZnTe) may also be used. The THz detector 110 is coupled to the receive antenna and is also coupled to receive the delayed optical pulses from delay comprising optics 108 for synchronously detecting the THz or near THz radiation transmitted by the sheet material sample 130. The detector 110 generates electrical detection signals. Although FIG. 3 shows a THz focused beam interacting with the sample 130, it is understood that other optical geometries such as a collimated geometry can also be used.

A signal processing system 125 is coupled to the detector 110 to receive the electrical detection signals. The signal processing system 125 comprises memory 126 Signal processing system 125 also includes processing electronics 128 that generally includes a transimpedance (current to voltage)-amplifier, filter and analog to digital (A/D) converter. A processor 127 receives processed electrical signal (amplified, filtered and converted to a digital signal) from processing electronics 128. The processor 127 can combine a signal associated with the transmitted pulse together with the calibration data and a reference signal pulse to determine at least one property of the sheet material sample selected from the moisture content, basis weight and caliper.

With respect the reference pulses and to techniques for applying the correction, processor 127 in signal processing system 125 can compare the continuous set of reference pulses with sample pulses and execute the necessary corrections for time jitter and amplitude variations. In particular, process 127 calculates the sample and reference measurement data for the coated web sample and is programmed to compare the sample measurement data to the reference measurement data. By iteratively assigning values for the thickness of the coating and the thickness of the substrate layer based on the analytical model of the coated continuous web a best fit relationship between the sample measurement data and the reference measurement data is achieved to calculate the caliper of the coating.

The detection electronics generally utilizes a lockin detection scheme (not shown) in which a modulated bias voltage is applied to the transmitter antenna. This modulation signal is also fed to lock-in detection electronics that increases the signal-to-noise ratio of the system as well as minimizes the effect of any background signal. A mechanical chopper can be used in the source femtosecond laser beam 105 to realize the lock-in detection—in the case a DC bias voltage is applied to the antenna.

In implementing the inventive technique for measuring caliper coatings, the refractive indices of the measured materials (base and coating) are determined from published data or they can be measured with a conventional device. In addition, it may be useful to add another sensor to measure a specific parameter of the base layer (or any other layer). For instance, an infrared gauge can be use to measure the moisture of the base material to correct the refractive index.

Thereafter, the reference measurement is taken wherein no sample in used in device 10 for generating continuous referencing shown in FIG. 2. The reference signal may be corrected using the Z-sensor signal. The coated, traveling continuous web is positioned between the gap of the device and sample measurements are taken. Measure signals from the detector are captured and saved for future analysis. The measure signal may be corrected using the Z-sensor signal. The fitting algorithm is applied in which the delay and amplitude of the measuring signal versus the reference signal and refractive indexes of materials are used in the algorithm to determine the thickness of the base and coating material. Thickness of the coating material is supplied as a result of the procedure.

Figure 4:
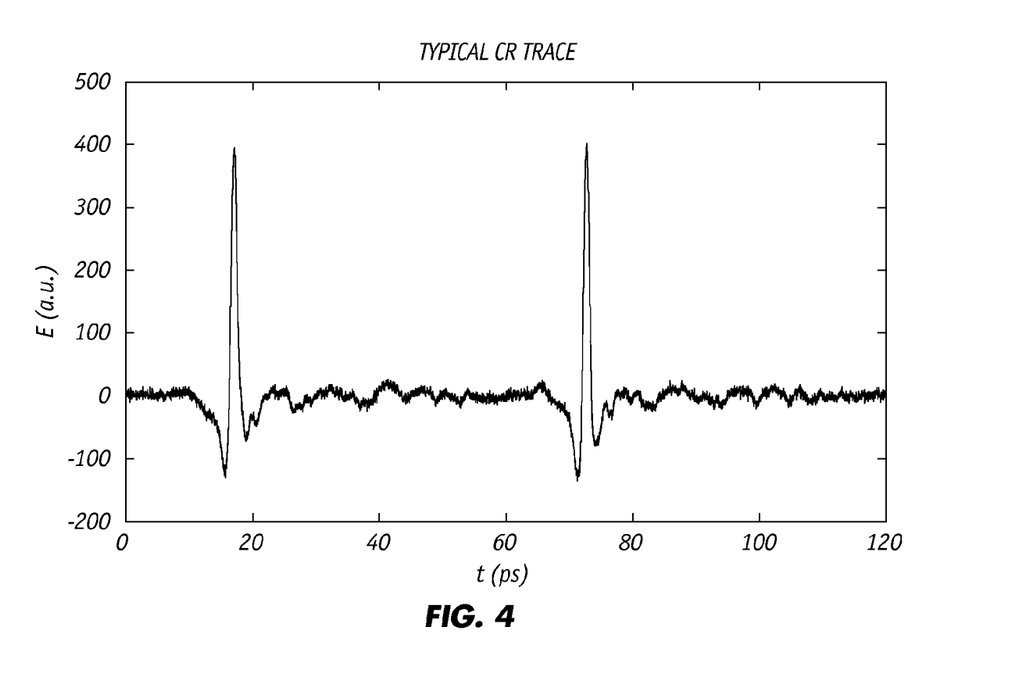
FIG. 4 shows a representative continuous CR trace generated by a beam splitter.

With THz-TDS transmission-based sheet measurement system 100 of FIG. 3, for each pulse that is generated by the emitter of the terahertz spectrometer, the beam splitter generates two pulses one that passes through the sample of interest and the other pulse traveling through air. FIG. 4 depicts two representative pulses that are formed by the beam splitter. Each pulse has a characteristic profile and peak and, the left pulse is designated the "left" pulse and the right one the "right" pulse. An arbitrary point somewhere in the middle to separate the two can be selected. In the above analysis, the "right" pulse is used both as a reference (i.e., where the pulse travels through air) and as a sample pulse (i.e., where the pulse travels through a sample). These are two separate measurements conducted one after the other.

One method of implementing the continuous referencing procedure is to initially collect a set of reference pulses. In this set, the two pulses ("left" and "right") travel through air. Thereafter, a sample of interest is inserted in one of the arms of the spectrometer (i.e., the right arm) and a new data set is collected. All analysis can now be performed using the reference and sample "right" pulse measurements. The left pulse is used to trace the changes in time and amplitude of the right pulse. Since any changes in the "left" pulse will most likely manifest in the "right" pulse, the "left" pulse could be monitored and used to correct the "right" pulse and thereby reduce the effects of jitter.

Figure 5:
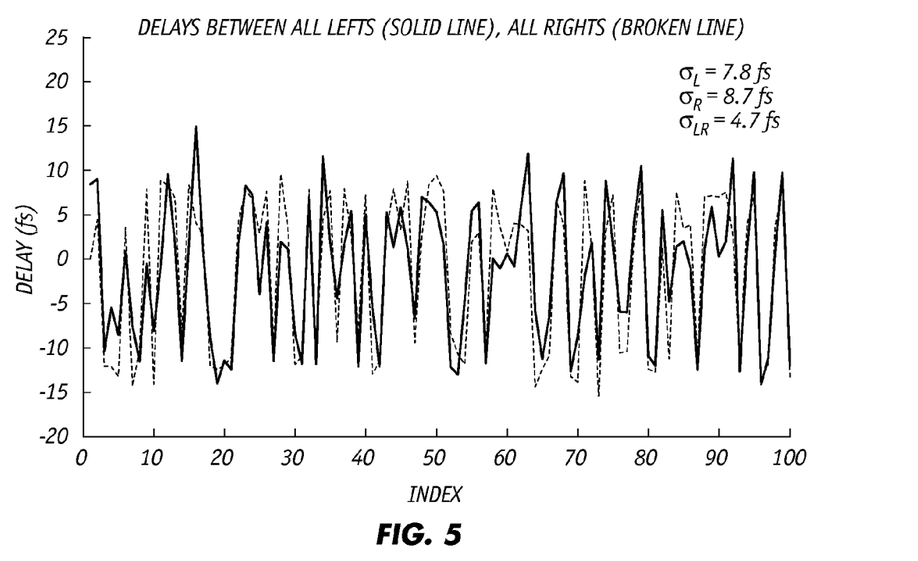
FIG. 5 compares the inter-pulse jitter between two sets of pulses.

FIG. 5 shows the inter-pulse time jitter between the "left" and "right" pulses for 100 different measured pulses. The "index" designation on the x-axis refers to the experiment measurement number (1-100) so that each point on the graph corresponds to a set of left and right pulses. The plot shows the pair wise time delay between the left and right pulses. This correlation plot further establishes that the two pulses move synchronously which permits the correction of time jitter in one of the pulses. The comparison demonstrates that the standard deviation of jitter could be reduced by a factor of 2.

Figure 6:
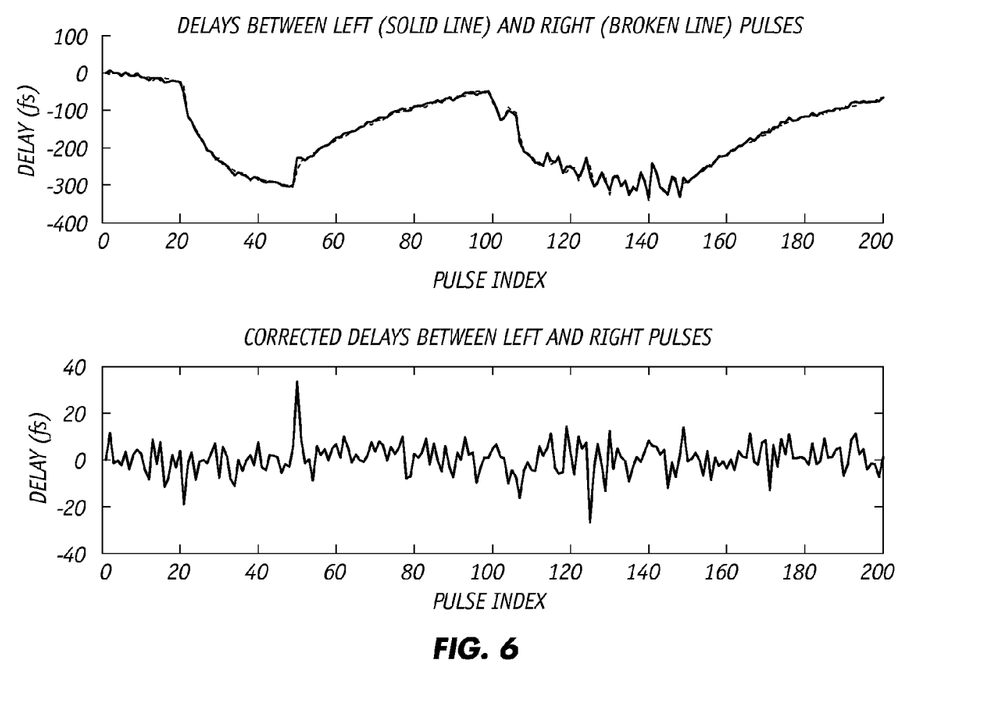
FIG. 6 are graphs that show the delays between two sets of pulses and corrected delays thereto.

For fiber optics based terahertz time-domain spectrometers where precise phase measurements are particularly critical, the continuous referencing procedure can compensate for the adverse effects of temperature and other factors that otherwise would interfere with phase measurements. In particular, for a fiber optics based spectrometer, a polarization and/or path length change occurs as a result of fibers being twisted or stretched that occurs with movement of the sensors as they scan the sample. The top plot of FIG. 6 is the inter-pulse time jitter between the "left" and "right" pulses for 200 different measured pulses as the fiber connections of the terahertz time-domain spectrometer were manually twisted to simulate the effects of movement for a scanning type system typically used in a paper machine. The plot shows that, the polarization change affects the delay of the pulses. The lower plot of FIG. 6 demonstrates that the inventive technique can be employed to track and correct these delays as the two pulses are affected similarly and one could be used to track the changes in the other.

Once the continuous set of reference pulses is obtained, the sample pulses' phase and amplitude can be tracked and corrected, as necessary. For example, time jitter can be corrected using the reference pulses by adding or subtracting a delay to the sample pulse. To correct for amplitude variations with the reference pulses, scaling of the sample amplitude by multiplicative factor can be used to increase or decrease its intensity.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A method of measuring the thickness of a coating on a coated continuous web that comprises the steps of:
    (a) developing an analytical model of the coated continuous web having one or more coating layers and a substrate layer wherein the model expresses the transmission of electromagnetic field through the coated continuous web as a function of (i) the thickness of each coating layer, (ii) the thickness of the substrate layer, (iii)

the refractive indices of each coating layer and of the substrate which values are initially assigned, and (iv) angle of incident of terahertz radiation onto the coated continuous web;

(b) establishing a sample measurement for a coated continuous web sample by employing a time-domain terahertz spectroscopy apparatus that includes an emitter that generates pulses of radiation and a detector that receives pulses of radiation, which comprises the steps of:

(i) positioning a beam splitter along an optical path between the emitter and the detector to form reference radiation pulses and sample radiation pulses that are directed to the sample and the reference radiation pulses do not interact with the sample;

(ii) positioning a first mirror to reflect sample radiation pulses to the detector; and (iii) positioning a second mirror to reflect reference radiation pulses to the detector and using the reflected radiation pulses to monitor fluctuations in phase and amplitude of the reference radiation pulses;

(c) establishing a reference measurement for the coated continuous web sample with the time-domain spectroscopy by executing steps (b)(i), (b)(ii) and (b)(iii) without placement of any sample for measurement; and (d) comparing the sample measurement to the reference measurement and iteratively assigning values for the thickness of the coating and the thickness of the substrate layers based on the model defined in step (a) so as to achieve a best-fit relationship between the sample measurement and the reference measurement to thereby determine the thickness of the coating.

2. The method of claim 1 wherein in step (b) the beam splitter is housed in a first module and the first mirror is housed in a second module and wherein the first and second modules define a gap through which a sample is positioned and wherein step (b) further comprises the step of measuring the distance between the modules and correcting the sample measurement to account for variations in the distance traveled by the sample radiation pulses.

3. The method of claim 1 wherein in step (b)(i) the sample radiation pulses are directed to the sample at a normal angle that is initially measured to select the desired analytical model for analysis.

4. The method of claim 1 wherein the analytical model of the coated continuous web is a four layer system that includes a first air layer, a coating layer, a substrate layer, and a second air layer.

5. The method of claim 1 wherein step (b) generates measurement signals that exhibit measurement delay and amplitude characteristics and step (c) generates reference signals that exhibit reference delay and amplitude characteristics and step (d) compares the measurement signals to the reference signals.

6. The method of claim 1 wherein the adjacent, layers exhibit different refractive indices.

7. The method of claim 1 wherein each layer in the coating or substrate layer is fabricated from material that is selected from the group consisting of paper, board, plastics, polymers, natural rubber, metals, natural fiber and synthetic fiber.

8. The method of claim 1 wherein in step (b) the reference and sample pulses from the beam splitter are separated in time so that the reference pulses reach the detector at different times relative to the sample pulses.

9. The method of claim 1 wherein step (b) further comprising correcting time jitter based on detection of the reference radiation pulses.

10. The method of claim 1 further comprises correcting amplitude variations based on detection of the reference radiation pulses.

11. An apparatus for analyzing a coated continuous web sample having one or more coating layers and a substrate layer to measure the thickness of a coating on the continuous web that comprises:

means for establishing sample measurement data for the coated continuous web sample that includes a time-domain terahertz spectroscopy device;

means for establishing reference measurement data for the coated continuous web sample that includes the time-domain terahertz spectroscopy device; and electronic data processing means programmed and operatively connected for processing the sample measurement data and the reference measurement data wherein the data processing means is programmed to compare the sample measurement data to the reference measurement data and iteratively assigning values for the thickness of the coating and the thickness of the substrate layer based on an analytical model of the coated continuous web so as to achieve a best fit relationship between the sample measurement data and the reference measurement data to thereby determine the thickness of the coating.

12. The apparatus of claim 11 wherein the time-domain spectroscopy device comprises:

an emitter that generates pulses of radiation;

means for splitting the pulses of radiation to yield reference radiation pulses and sample radiation pulses wherein the sample radiation is directed to the sample and wherein the reference radiation pulses do not interact with the sample;

a first mirror positioned to reflect sample radiation that has been transmitted through or reflected from the sample;

a second mirror positioned to reflect the reference radiation pulses; and a detector positioned for receiving the reflected reference radiation pulses and the reflected sample radiation pulses, with the proviso that the means for establishing the reference measurement data does not use a sample.

13. The apparatus of claim 12 wherein the means for splitting the pulses of radiation comprises a beam splitter.

14. The apparatus of claim 13 wherein the reference and sample pulses from the beam splitter are separated in time so that the reference pulses reach the detector at different times relative to the sample pulses.

15. The apparatus of claim 12 wherein the reference and sample pulses are measured using a single detector.

16. The apparatus of claim 12 further comprising means for correcting time jitter based on detection of the reference radiation pulses.

17. The apparatus of claim 12 further comprising means for correcting amplitude variations based on detection of the reference radiation pulses.

18. The apparatus of claim 12 wherein the first mirror is positioned to reflect sample radiation that has been transmitted through the sample.

19. The apparatus of claim 11 comprising means for measuring the refractive index of the coating layers or substrate.

20. The apparatus of claim 12 wherein in the beam splitter is housed in a first module and the first mirror is housed in a second module and wherein for the means for establishing the sample measurement data the first and second modules define a gap through which a sample is positioned and wherein the means for establishing the sample measurement data measures the distance between the modules and correcting the sample measurement to account for variations in the distance traveled by the sample radiation pulses.

* * * * *